United States Patent [19]

Lauks

[11] Patent Number: 4,998,881

[45] Date of Patent: Mar. 12, 1991

[54] DEVICE AND METHOD FOR PRODUCING IMPLANT CAVITIES

[76] Inventor: Nikola Lauks, Saalkamp 8, 2000 Hamburg 65, Fed. Rep. of Germany

[21] Appl. No.: 304,365

[22] Filed: Jan. 30, 1989

[30] Foreign Application Priority Data

Jan. 29, 1988 [DE] Fed. Rep. of Germany ....... 3802789

[51] Int. Cl.$^5$ ................................................. A61C 8/00
[52] U.S. Cl. ...................................... 433/173; 433/75; 433/76
[58] Field of Search ..................... 433/75, 76, 165, 173

[56] References Cited

U.S. PATENT DOCUMENTS

| 1,447,774 | 3/1923 | Fortunati | 433/75 |
| 2,653,385 | 9/1953 | Kay | 433/76 |
| 3,078,580 | 2/1963 | Galvez | 433/76 |
| 3,226,828 | 1/1966 | Spalten | 433/76 |
| 3,407,503 | 10/1968 | Nealon | 433/76 |
| 3,508,334 | 4/1970 | Weissman | 433/76 |
| 4,568,285 | 2/1986 | Chiaramonte et al. | 433/173 |
| 4,787,848 | 11/1988 | Ross | 433/165 |
| 4,820,159 | 4/1989 | Weissman | 433/165 |

FOREIGN PATENT DOCUMENTS 853645  11/1960  United Kingdom ............... 433/165

*Primary Examiner*—John J. Wilson
*Assistant Examiner*—F. LaViola, Jr.
*Attorney, Agent, or Firm*—Herbert Dubno

[57] ABSTRACT

Implant cavities are drilled in the jaw of a patient by first forming a template from a plastic cast of an impression of the jaw regions after it has been prepared as for parallel-crown preparation and the template is provided with parallel bores in which slide sleeves guiding the drill bit of the drill can be received.

24 Claims, 8 Drawing Sheets

DEVICE AND METHOD FOR PRODUCING IMPLANT CAVITIES

FIELD OF THE INVENTION

My present invention relates to a drilling device for jaw surgery and, particularly, for the formation of implant cavities in a jawbone as part of a dental surgical procedure for anchoring an implant in a jawbone. The invention also relates to a method of forming the implant cavities.

BACKGROUND OF THE INVENTION

In various dental surgical procedures, jaw surgery in general and work with oral implants, it is a common practice to insert a cylindrical implant into a bore or implant cavity provided for this purpose in the jawbone of a patient.

A number of problems have been encountered in connection with the drilling of such cavities and indeed, these problems can be so severe that in some cases the use of implant techniques must be discarded since there are no anatomical conditions in which a satisfactory attachment of the implant can be guaranteed. Such cases include, for example, the lack of sufficient bone substance for an implant cavity.

However, even when there is sufficient bone substance for an implant cavity, problems have been encountered in the past in forming the implant cavity with a sufficient degree of precision and parallelity, especially where a number of implant cavities are required in a certain region of a jawbone.

Usually such bores are formed in a freehand manner in the jawbones. Of course, this can readily result in defective bores. An especially great danger is the drilling of the bore to an excessive depth so that the Sinus Maxillaris or the Canalis Mandibularis is trepanned.

Of course, there is also a danger that the bore will be at such an inclination that the spongiosa will be excessively damaged in the transverse direction. Such damage can result in jaw resorption. The importance of the transverse dimension is that with implantation, one should ensure a thickness of about 1 mm of spongiosa between an implant and the laminar externa and interna of the respective jaw structure to ensure a sufficient blood supply around the implant and hence growth of bone tissue around the implant to anchor it.

Failure to maintain precision with respect to this dimension has been found to be the cause of a variety of problems.

It has been found that especially later, when the implant is subjected to loading and when the implants are not exactly parallel to one another or to the teeth, that there is a vertico transverse pressure transmission to the implant.

This vertico transverse loading provides a pressure effect on one side of the implant and a tension effect on the opposite side.

Both effects increase, over extended periods, the bone resorption effect and give rise to a funnel-shaped bone resorption pattern which can produce secondary infections around the implant.

OBJECTS OF THE INVENTION

It is the principal object of my invention to provide a drilling device for the purposes described which can provide highly precisely-placed and accurately-dimensioned implant cavities in jaw regions, even where the space for such cavities is greatly limited and whereby drawbacks of the prior art are avoided.

Another object of the invention is to provide an improved method of forming such implant cavities with a high degree of parallelity and dimensional precision in a jawbone of the patient.

SUMMARY OF THE INVENTION

These objects and others which will become apparent hereinafter are attained, in accordance with the invention, in a method of forming implant cavities in a jawbone of a patient which comprises:

(a) grinding residual teeth correspondingly to parallel clinical crown preparation in the region;

(b) forming an anatomically correct impression of the region;

(c) casting a model of the anatomically correct impression;

(d) modelling of a hardenable synthetic resin in a plastically deformable form, a template of the region on the model; and (e) using the template as a guide, drilling cavities in the jaw bone of the jaw region of the patient.

The instrument, device or apparatus provided for this purpose can then comprise:

a drill provided with a boring tool;

a guide sleeve receiving the tool and slidably guiding the tool along an axis of the guide sleeve; and a guide-sleeve template conforming in shape to a shape of a jaw region of a patient to receive an implant and holding the guide sleeve for positioning the guide sleeve in the jaw region of the patient.

According to the invention, therefore, the drill bit or tool passes through a slide bore bushing or sleeve to penetrate into the jawbone with this sleeve being held in place by a boring sleeve template which has previously been fabricated to correspond to the shape of the jaw region and has been held on the jaw region to act as a guide for the sleeve which, in turn, forms a guide for the drilling tool or bit mounted in a drill head, preferably an angled drill head in which the drive shaft is at an angle to the shaft of the chuck or holder for the drill bit.

Through the use of a template and sleeve which can be removably received in a throughgoing hole in the template, and a slider on the drill which connects the sleeve to the latter, I am able to effect a three-dimensional proportion of an implant cavity as well as an exact localization thereof in a particular region of a jawbone.

The danger of loss of spongiosa or an injury to the patient is practically completely excluded.

Depending upon the anatomical requirements, the invention allows a plurality of implants to be implanted with exact parallelism to one another while also satisfying all of the three-dimensional requirements for location and positioning of the implant cavities.

Since the parallelity and positioning is determined by the template which is modeled on a plastic cast of the mouth region, the parallelism of the cavities and the ability to locate them topographically with precision and preplanning enables the technique to be used for a wide variety of prosthetic needs. For example, it can be used for mounting a bridge or pin prosthesis even in the presence of intact teeth or other bridges or crown structures.

Because of the high degree of parallelity, moreover, the aforementioned vertico transverse loading which could have traumatic effect upon the implanted pin or bridge does not arise and the danger of loosening of the implant is greatly reduced or entirely eliminated.

The slide sleeve is provided on the hand-drill or the angle piece of the drilling apparatus and serves, in addition, to limit the depth to which the cavity is drilled. The sleeve itself may form a stop for a shoulder on the drilling bit or tool and has an annular flange for this purpose which comes to rest on the surface of the template.

The invention also relates to a method of fabricating the drilling sleeve template for use in the fabrication of an implant cavity.

The drilling can be effected on a parallelometric table, for example. A precondition for the accurate parallel positioning of one or more implant cavities, therefore, is the fabrication of a sleeve template to conform to the region of the jawbone in which the cavities are to be drilled so that the template will be available as a precise guide for the sleeve in which, in turn, the drill bit is guided.

The residual teeth of the patient in this region are subjected to the customary clinical preparation for parallel crowns and an anatomical implant is then taken of the prepared region including the teeth which have so prepared and spaced between these teeth. This impression is then used to prepare a cast, generally of plaster and hereinafter referred to as a model. The template body is then formed on this model from a plastic hardenable synthetic resin. Following hardening, the template can be used in the manner described.

BRIEF DESCRIPTION OF THE DRAWING

The above and other objects, features and advantages of the present invention will become more readily apparent from the following description, reference being made to the accompanying drawing in which.

SPECIFIC DESCRIPTION

Figure 1:
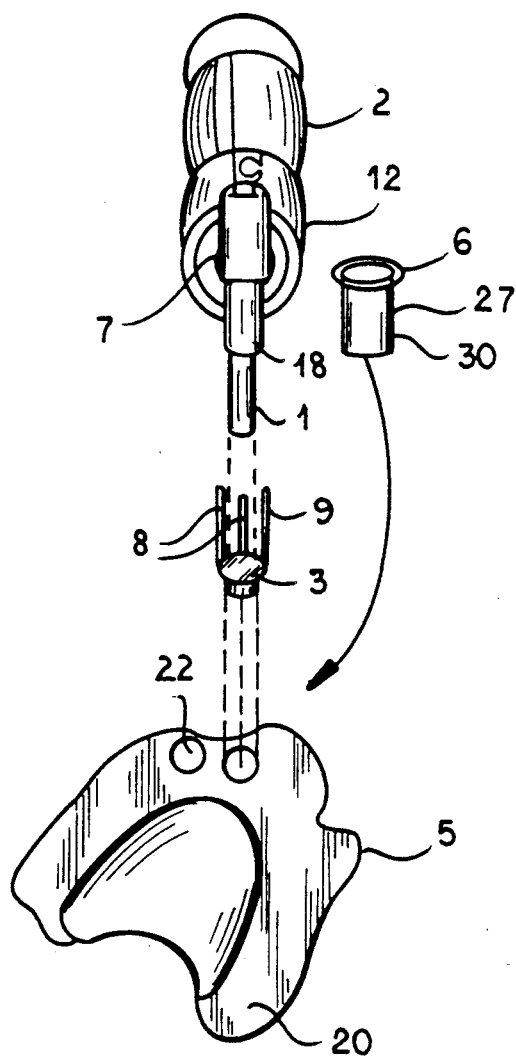
FIG. 1 is a perspective view of a drilling apparatus provided with the angle piece, a slidable boring sleeve and slider, and a template, a precision sleeve being likewise illustrated and serving for purposes to be described hereinafter.

The apparatus for producing implant cavities in a jawbone, according to the invention, comprises a drill bit 1 which is rotated by an angle drive represented generally at 2 and is guided in a slide sleeve 3 through which the drill bit can extend and which, in turn, is held on the jawbone 4 of the patient by a drill sleeve template represented at 5.

The slide sleeve 3 is substantially of cylindrical shape and has an inner diameter corresponding substantially to the outer diameter of the drill bit or tool 1.

At its side turned toward the angle piece 2, the slide sleeve 3 is formed with a radially extending annular flange 6 connected to or forming part of a slide 7 guided on the angle piece 2.

The slide 7 guides the sleeve for movement along the drill parallel to the axis of rotation of the drill bit or tool 1.

Figure 2:
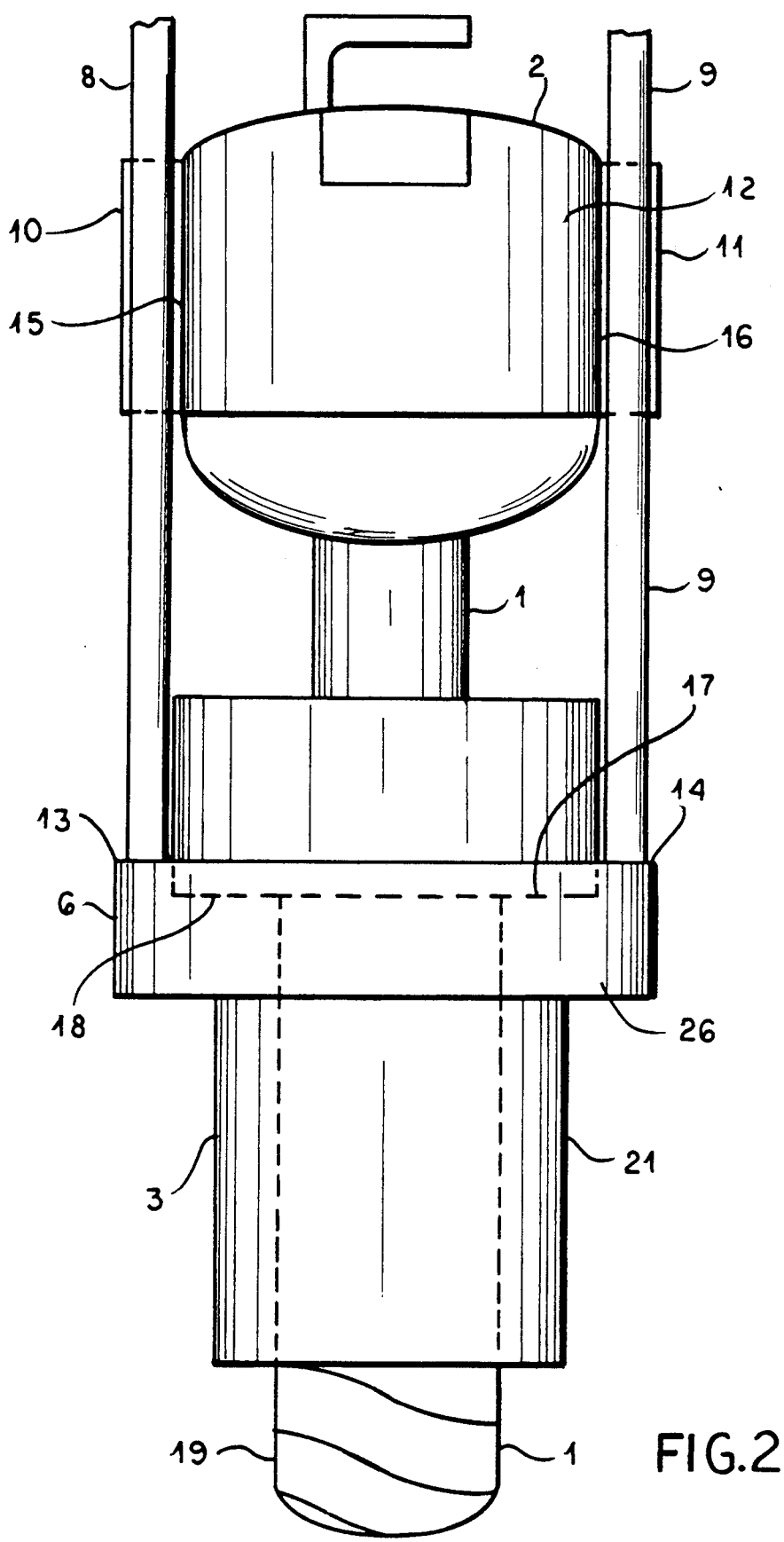
FIG. 2 is a front view of the drilling apparatus in which the drill bit or tool has passed fully through the guide sleeve.

The slide 7 has two guide rods 8, 9 which are affixed at opposite regions 13 and 14 to the flange 6 as can be seen in FIG. 2, although three such rods can be provided in angularly equispaced relationship as will be apparent from FIG. 1.

The guide rods 8 and 9 extend parallel to the rotation axis of the drill bit 1 and are guided in respective U-section guides or channels 10 and 11 affixed at opposite lateral flanks 15 and 16 of the attachment element or chuck 12 of the drill head.

The U-profiles 10 and 11 are thus disposed parallel to one another and, of course, to the axis of the drill bit 1.

The slide sleeve 3 is provided in the region of the flange 6 with an annular abutment or stop surface 17 which can engage a shoulder 18 of the drill bit to form a depth stop establishing a predetermined penetration depth of the drilling crown 19 of the drill bit 1.

To allow a variety of cavity depths to be made, a corresponding number of drill bits 1 is provided with the respective drill crowns or shanks 19 and stops 18 appropriately dimensioned to provide various drilling depths. In all cases, the dimensions of the annular flange 6 and the spacing between the underside 26 of the sleeve 3 and the abutment surface 17 can be used to define the depth of drilling of each cavity.

The sleeve 3 is replaceably fixed on the template 5. The latter is constituted as a plate of synthetic resin forming a template body 20 which can be conformed to a plaster model of the jaws 4 of the patient, the plaster model, in turn, being cast from an impression taken of the jaw.

Figure 3:
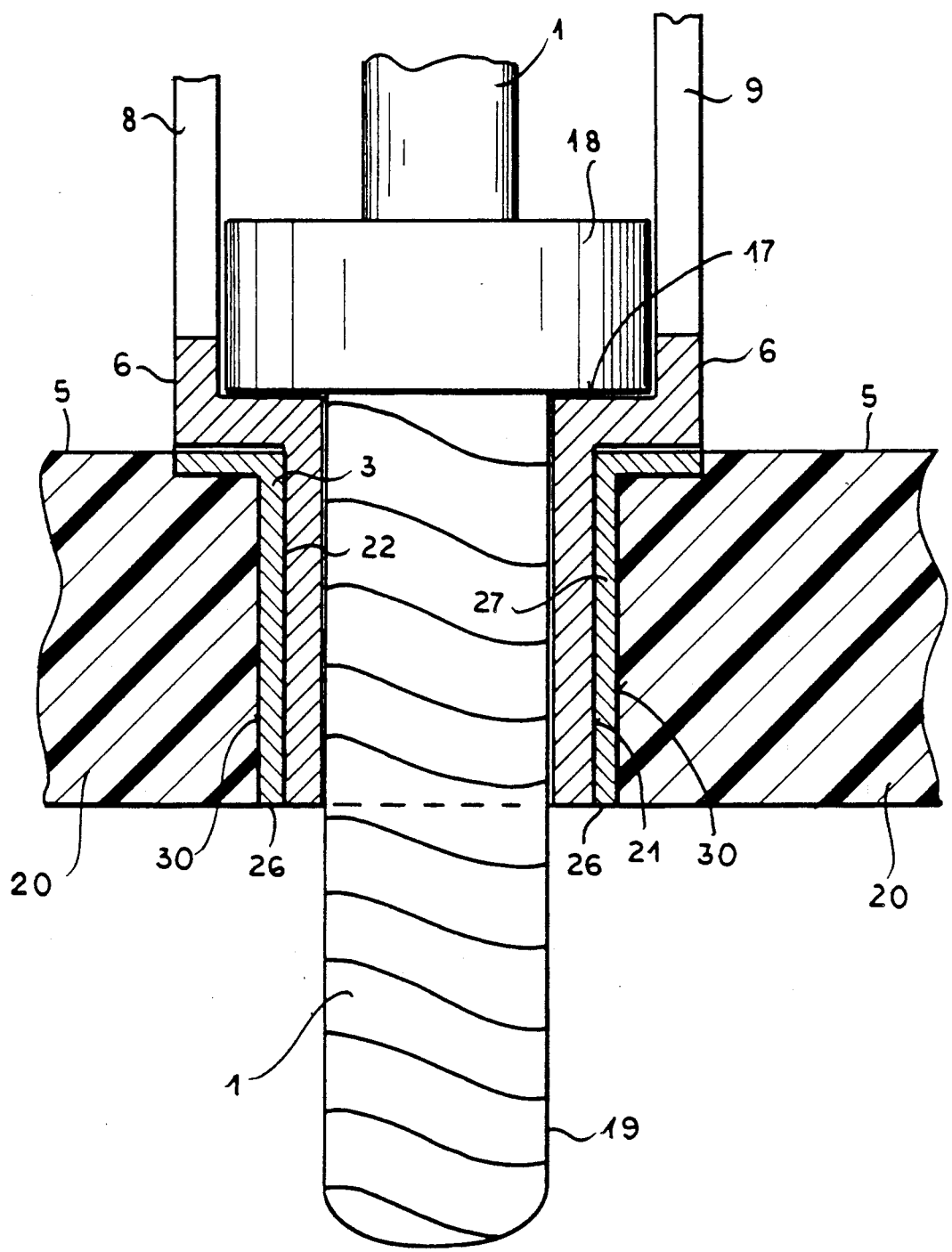
FIG. 3 is a cross sectional view of the guide sleeve and the template showing its relationship with the drill bit.

The template 5 has a thickness which corresponds substantially to the axial height or length of a cylindrical region or shank 21 of the sleeve 3 projecting downwardly in FIG. 3 or the flange 6.

The boring slide sleeves 3 are guided into and positioned by cylindrical bores 22 in the template 5 into which precision sleeves 27 have been fastened and which snugly fit and engage the cylindrical regions 21 of the boring sleeves 3 to hold and guide them in parallel relationship. This retention and guidance is effected between the precisely bored cylindrical inner wall of the precision sleeve 27 and the cylindrical outer wall of the region 21 of the boring sleeve 3 in which, in turn, the drill bit is guided.

The cylindrical region 21 and the precision sleeve 27 have their diameters so matched that between the cylindrical region 21 and the precision sleeve 27, there is a friction fit ensuring precise relative displacement, i.e. displacement without lateral play.

The template 5 is provided with cylindrical bores or holes 22 tight-fittingly receiving the cylindrical regions 21 of the sleeves 3. The sleeves, when positioned in these bores, or a sleeve when inserted into each of these holes 22, is thus always parallel to the sleeves inserted into the other holes.

It is also possible, according to an embodiment of the invention, which has not been illustrated, to provide the slide 7 with a single guide rod 8 which is slidingly received in a U-profile 10. In this case, the rod 8 and the U-profile 10 are form-fittingly engaged to prevent relative rotation of the rod and the guide.

Instead of U-profiles 10 and 11 it is also possible to provide closed sleeves in which the guide rods can slide. Finally it is possible to form the slide 7 as a metal sleeve whose inner diameter corresponds to a cylindrical outer diameter of the chuck or other receiver 12 for the drill bit 1 of the drilling machine.

The method of forming the implantation cavities has been previously described. However, the method of making the template is accomplished by the following steps.

In the region at least at which implantation cavities are to be formed on a jaw of the patient, the remaining teeth of the patient are prepared by the techniques used for parallel clinical crown preparation.

An anatomical impression is then taken of the region and from the anatomical impression using wax or other plastic material, a plastic cast is made.

Figure 4:
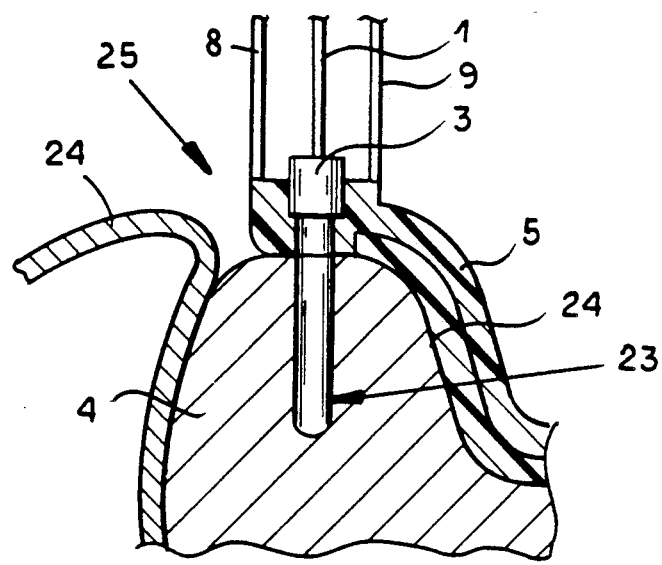
FIG. 4 is a diagrammatic cross sectional view of the jawbone showing the formation of the implant cavity therein.
Figure 5:
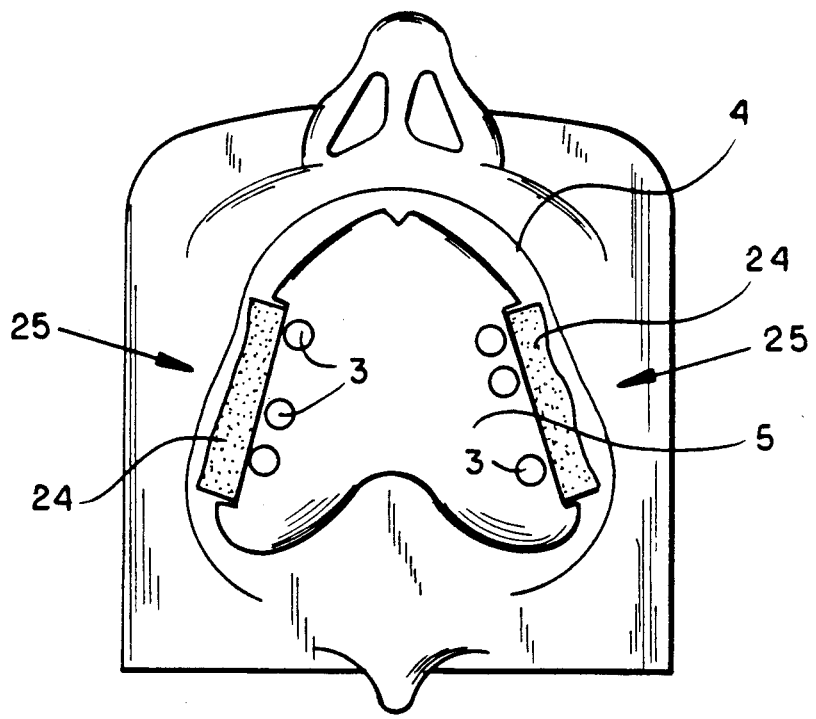
FIG. 5 is a diagrammatic view of the underside of the upper jaw of a patient showing the location of implant cavities formed therein.
Figure 6:
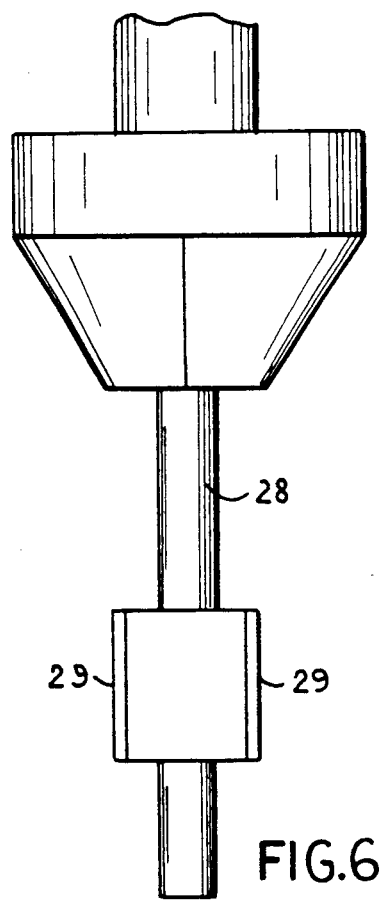
FIG. 6 is a side elevational view of the chuck or clamp head of a parallelometer with a guide pin for a slidable boring sleeve.

In a parallelometer, the parallelity of the teeth is tested. If parallelity is achieved, the template 20 is modeled on the plaster body from a plastically deformable but hardenable synthetic resin. The template body is so formed that upon application thereof to the jaw, the submucosa 24 will not be damaged, nor will there be an adverse effect on the gums or other mouth tissues. The template body 20, of course, must also be shaped for the operation field 25 (see FIGS. 4 and 5).

When the template body 20 is hardened, at each location at which an implant cavity 23 is to be drilled in the jawbone of the patient, a hole 22 is bored.

To this end, the model is provided with the equivalent bores beforehand by being clamped on a parallelometric table of a milling machine which ensures that the bores which will ultimately correspond to the implant cavities 23 will be exactly parallel.

With this drilling, which should correspond to the thickness of the implant and can have a diameter of 4 or 3.3 mm, for example, I can control on the model, the distance the spongiosa is from the implant to the lamina externa and the lamina interna of the patient.

If at the location at which the implant is to be seated there is an ostosis, the model can be smoothed correspondingly so that the template region will have a wide drilling plateau in which to accommodate the slide sleeve 3.

The prebored hole in the template body 20 can be enlarged to a diameter of about 7 mm so that a region 30 of a precision sleeve 27 turned toward the template body 20 and having a diameter of about 6 mm will provide a sufficient play to allow offsetting as required should the distances between the implant cavity and the lamina interna and lamina externa have been chosen incorrectly.

The precision sleeve 27 can be fixed by initially mounting the model together with the template body 20 and the parallelometer table in the parallelometer. In place of the parallelometer pin, a guide pin 28 with U-section guides 29 is clamped, the U-profiles 29 corresponding in form to the U-profiles 10 and 11 on the angle piece 2 and which form the slide arrangement with the guide rods 8, 9 on the slidable drilling sleeve 3.

Upon the guide pin 28, a drilling sleeve 3 upon which has been mounted a precision sleeve 27, is placed and the sleeves 27 and 3 are then inserted into the corresponding hole with enlarged diameter in the template body 20 and the model by the pin until the precision sleeve 26 comes to rest with lower surface against the upper surface of the model.

Any inaccurate positioning of the precision sleeve 27 can be corrected on the parallelometer and the precision sleeve 27 held in place until it is bonded in its final position by a simplex synthetic resin.

After the autopolymerization of the synthetic resin, the drill guide sleeve 3 can be withdrawn from the precision sleeve 27, now firmly anchored in the template, and only reinserted as cavity- -drilling requirements warrant.

Depending upon the number of implant cavities 23, the process can be repeated so that respective sleeves 3 can be provided in each hole of the template or in each of the precision sleeves 27 thereof. Of course a single drill-guide sleeve can be used and can be inserted in the holes 22 or the precision sleeves 24 in succession. The template 5 is placed on the jaw region 4 of the patient after the operation field has been prepared by removing gum tissue and submucosa 24, in a flap from the region to be drilled by the use of different bores 2 with increasing diameter and respective slide sleeves 3, implant cavities 23 can be drilled with exact polarity to any desired diameter without any risk of injury of the patient.

The drilling, of course, is as precise as the fabrication tolerances of the various parts will allow and, of course, as precise as the model and x-ray evaluations can determine.

It has been found that it is not necessary, in the course of the operation, to flap over the gum tissue and submucosa. In the latter case, the implant cavity is drilled through the gum tissue and the submucosa. This results in a reduction in pain and the danger of infection.

Figure 7:
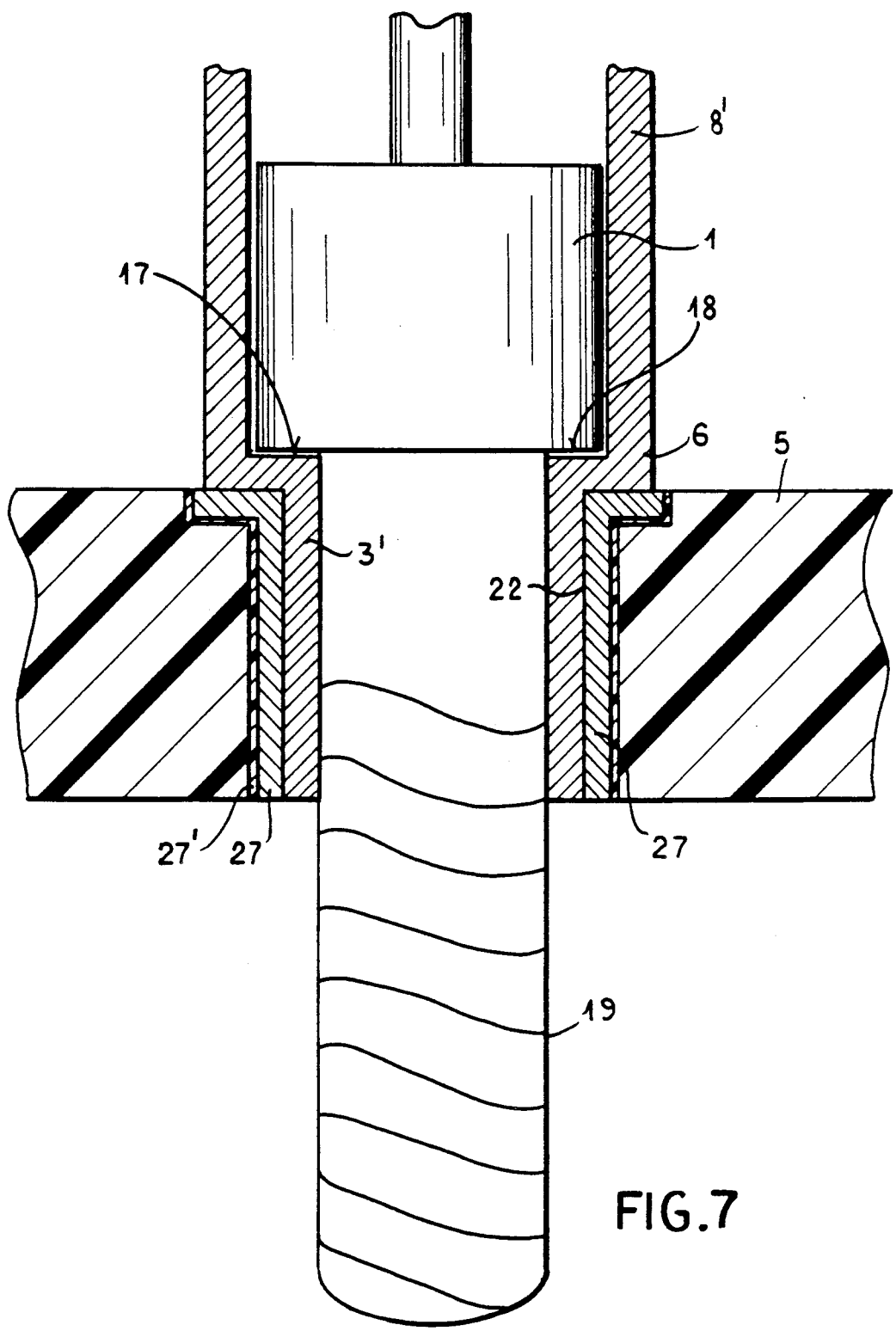
FIG. 7 is an axial section illustrating an embodiment of the invention wherein the tool guide sleeve forms part of a slider with a cylindrical structure rather than a plurality of rods or a single rod.

FIG. 7 illustrates an embodiment of the invention wherein, in place of the rods 8 and 9 of the embodiment of FIGS. 1–3, a tube or sleeve 8' is guided on a cylindrical nose or chuck portion of the angle piece (not shown) as part of the slider which is formed with the tool guide bushing 3'. Otherwise the apparatus of FIG. 7 operates in the manner described. In this embodiment, moreover, the precision guide sleeve 27 for the tool guide sleeve 3 is shown in place and bonded to the remainder of the synthetic resin template body 5 by the simplex synthetic resin 27'.

Figure 8C:
FIG. 8C is an elevational view of the tool.
Figure 8D:
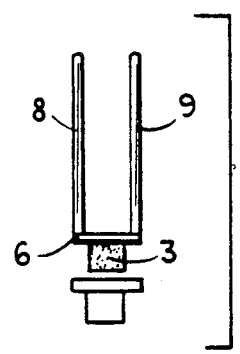
FIG. 8D is an exploded view illustrating a relationship of the tool guide slider to the precision bushing.
Figure 8A:
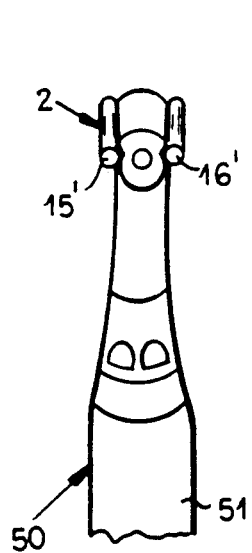
FIG. 8A is a front elevational view of the angle piece used in accordance with the invention.
Figure 8B:
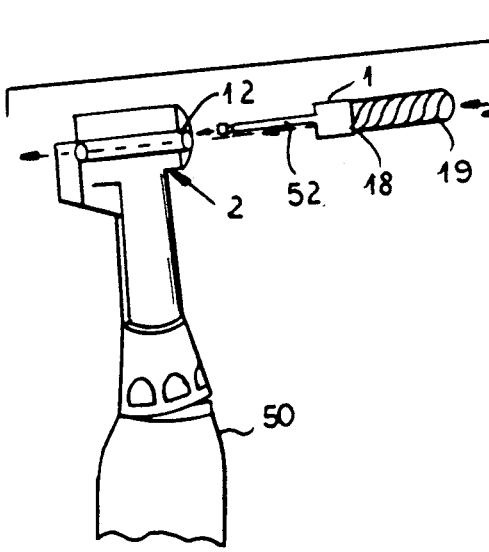
FIG. 8B is an exploded side elevational view of the angle piece and the slider and tool assembly.

FIGS. 8A and 8B show the angle piece 2 as the head of a conventional dental-surgery tool 50 with its handle 51. The turban drive for the tool is contained in the head and is conventional.

The tool 1 is shown in greater detail in 8B and can be seen to comprise, in addition to the cutting shank 19 and the shoulder 18, a shank 52 which can be fitted into and driven by the chuck portion 12 of the tool 50 (see also FIG. 8C).

FIG. 8D shows in greater detail the relationship between the tool guide bushing 3, the diametrically opposite rods 8 and 9 attached to the flange 6 thereof and precision bushing in which the guide sleeve 3 can be received with a friction fit, i.e. without lateral play, for accurate positioning of the boring tool in the formation of the implant cavity and for anchoring of the precision sleeve 27 in the body of the template 5 as previously described.

Figure 9:
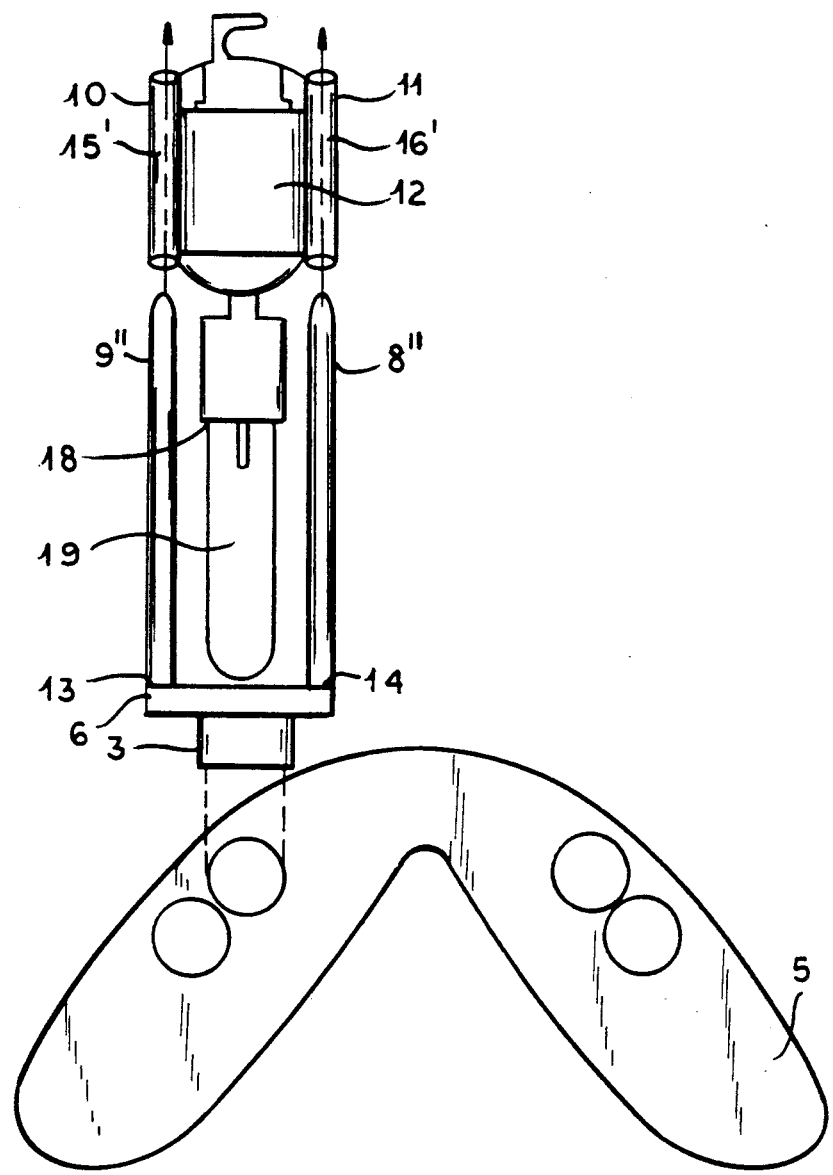
FIG. 9 is another diagram similar to FIG. 1 but wherein tubular guides are provided on the angle piece for the rods connected to the tool guide slider.

In FIG. 9, I have shown that the rods 8″ and 9″ connected to diametrically opposite sides 13 and 14 of the flange 6 of the tool guide sleeve 3 can be guided, not in U-section guides or channels on the head 2, but rather in tubes 15′, 16′ attached to opposite faces of the tool head 2 (see also FIG. 8A).

Figure 10:
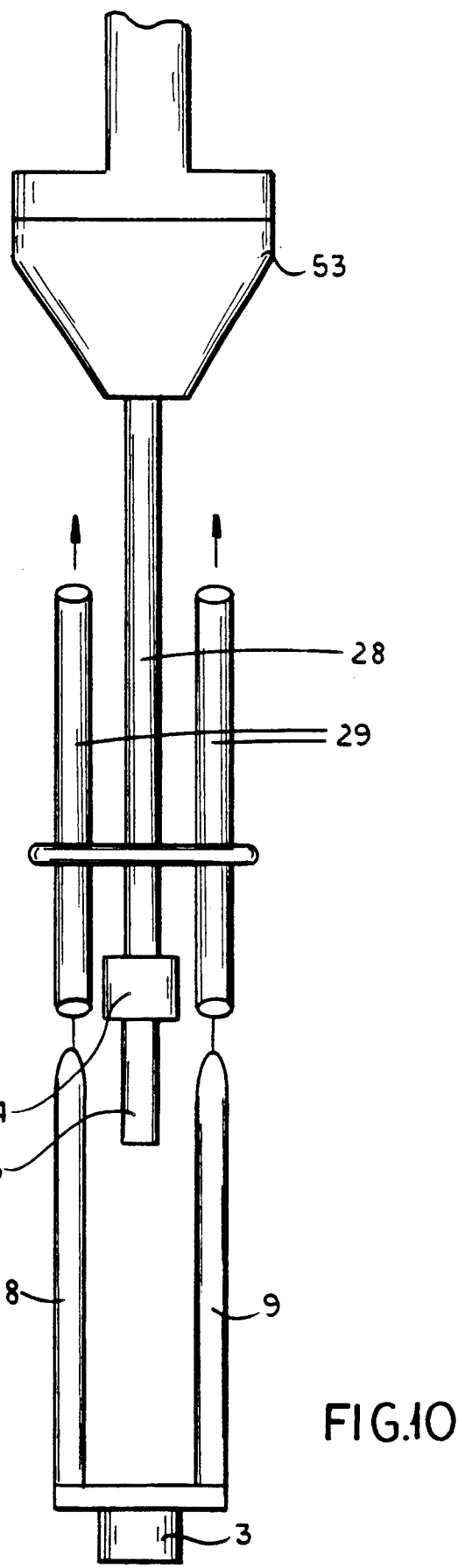
FIG. 10 is a diagrammatic illustration of a parallelometer used as a guide for the slider and a precision sleeve as described.

FIG. 10 illustrates the relationship between the parallelometer chuck or collet 53 and the guide pin 28 which can be substituted, according to the invention, for the normal parallelometer pin and has a shoulder 54 adapted to form a stop for the guide sleeve 3 which has the rods 8 and 9 previously described. A stem 55 of the pin 28 fits snugly in the interior bore of the sleeve to accurately position the latter, while precise positioning is further ensured by a pair of guide tubes 29 mounted on the pin 28 and respectively receiving the rods 8 and 9. The precision sleeve 27 is then fitted onto the guide sleeve 3 (see FIG. 8D) and the parallelometer used to position the precision sleeve 27 in the slight clearance in the template 5 for bonding in place.

I claim:

1. A jaw-surgery instrument for boring implant cavities, comprising:
   a drill provided with a boring tool;
   a guide sleeve receiving said tool and slidably guiding said tool along an axis of said guide sleeve;
   a guide-sleeve template conforming in shape to a shape of a jaw region of a patient to receive an implant and holding said guide sleeve for positioning said guide sleeve in said jaw region of the patient, said guide sleeve being formed with an end turned toward said drill and an end turned away from said drill and received in said template, said end turned toward said drill being formed with a radially outwardly extending annular flange; and
   a slide extending upwardly from said annular flange and guiding said drill relative to said guide sleeve.

2. The jaw-surgery instrument for boring implant cavities defined in claim 1 wherein said guide sleeve is substantially cylindrical and has an inner diameter corresponding substantially to an outer diameter of said tool.

3. The jaw-surgery instrument for boring implant cavities defined in claim 1 wherein said slide guides said drill along a path parallel to said axis.

4. The jaw-surgery instrument for boring implant cavities defined in claim 1 wherein said slide includes at least one guide rod extending parallel to said axis, said drill having channels in a form selected from the group consisting of a U-shaped member and a closed sleeve, said drill being thereby guided along said rod.

5. The jaw-surgery instrument for boring implant cavities defined in claim 4 wherein said guide rod is secured to said flange and extends therefrom to said drill.

6. The jaw-surgery instrument for boring implant cavities defined in claim 4 wherein said U-shaped member is secured to said drill close to a receptacle on said drill for said tool.

7. The jaw-surgery instrument for boring implant cavities defined in claim 4 wherein said slide is formed with two parallel guide rods affixed to opposite regions of said flange and slidingly engaged by respective U-shaped members affixed to opposite lateral surfaces of said drill.

8. The jaw-surgery instrument for boring implant cavities defined in claim 4 wherein said slide is formed with three angularly equispaced parallel guide rods affixed to said flange and slidingly engaged by respective U-shaped members affixed at angularly equispaced locations to lateral surfaces of said drill.

9. The jaw-surgery instrument for boring implant cavities defined in claim 1 wherein said slide comprises a metal sleeve having an inner diameter corresponding substantially to an outer diameter of a receptacle for said tool formed on said drill.

10. The jaw-surgery instrument for boring implant cavities defined in claim 1 wherein said tool is provided with an outwardly projecting depth-setting stop, said guide sleeve being formed in a region of said flange with an abutment surface engageable by said depth-setting stop.

11. The jaw-surgery instrument for boring implant cavities defined in claim 10 which comprises a set of tools interchangeable in said drill and having boring portions of different lengths as measured with respect to said stop.

12. The jaw-surgery instrument for boring implant cavities defined in claim 1 wherein said guide sleeve is replaceably held in said template.

13. The jaw-surgery instrument for boring implant cavities defined in claim 1 wherein said template is a body of synthetic resin conforming in shape to a plaster model constructed to correspond to said jaw region of the patient.

14. The jaw-surgery instrument for boring implant cavities defined in claim 1 wherein said template has a thickness corresponding substantially to an axial length of a cylindrical shank of said guide sleeve extending from said flange.

15. The jaw-surgery instrument for boring implant cavities defined in claim 1 wherein said template is formed with a plurality of holes adapted to receive said guide sleeve so that the axes of the guide sleeve in said holes are parallel to one another.

16. The jaw-surgery instrument defined in claim 15 wherein each of said holes has a precision sleeve fixed therein and of an inner diameter matching an outer diameter of a cylindrical region of said guide sleeve to form a friction fit therewith.

17. A method of boring implant cavities in a jaw bone of a jaw region of a patient, comprising the steps of:
   (a) grinding residual teeth correspondingly to parallel clinical crown preparation in said region;
   (b) forming an anatomically correct impression of said region;
   (c) casting a model of said anatomically correct impression;
   (d) modelling of a hardenable synthetic resin in a plastically deformable form, a template of said region on said model;
   (e) using said template as a guide for drilling cavities in the jaw bone of the jaw region of the patient; and
   (f) drilling holes with a drill in said template at locations at which said cavities are to be provided, whereby a guide sleeve for boring said cavities is inserted in at least one of said holes, said guide sleeve being formed with an end turned toward said drill and an end turned away from said drill and received in said template, said end turned toward said drill being formed with a radially outwardly extending annular flange, and said annular flange having a slide secured thereto extending upwardly and guiding said drill relative to said guide sleeve.

18. The method defined in claim 17 wherein said holes are drilled by milling on a parallelometer table.

19. The method defined in claim 17 wherein said model is smoothed in the region of a respective hole.

20. The method defined in claim 17 wherein a precision sleeve, whose inner diameter conforms to an outer diameter of the guide sleeve, is mounted in each of said holes.

21. The method defined in claim 20 wherein said guide sleeve carrying said precision sleeve is fed through a respective hole in said template until an underside of the precision sleeve turned toward the model abuts the model.

22. The method defined in claim 21 wherein said precision sleeve when positioned in said template establishes an optimal position of the respective guide sleeve in the template for a desired location of a respective cavity in the jaw bone of the patient, further comprising the step of bonding said precision sleeve in a cavity in said template with a simplex synthetic resin.

23. The method defined in claim 22 wherein a number of said precision sleeves are anchored in said template corresponding to a number of cavities to be drilled through said template in said region.

24. The method defined in claim 21 wherein said precision sleeve in mounted in said template on a guide pin on a parallelometer.

* * * * *